(12) United States Patent
Chaudry et al.

(10) Patent No.: US 6,702,997 B2
(45) Date of Patent: Mar. 9, 2004

(54) ALBUTEROL INHALATION SOLUTION, SYSTEM, KIT AND METHOD FOR RELIEVING SYMPTOMS OF PEDIATRIC ASTHMA

(75) Inventors: Imtiaz Chaudry, Napa, CA (US); Partha Banerjee, San Ramon, CA (US)

(73) Assignee: Dey, L.P., Napa, CA (US)

( * ) Notice: Subject to any disclaimer, the term of this patent is extended or adjusted under 35 U.S.C. 154(b) by 0 days.

(21) Appl. No.: 10/034,829

(22) Filed: Dec. 28, 2001

(65) Prior Publication Data

US 2003/0124063 A1 Jul. 3, 2003

Related U.S. Application Data

(60) Provisional application No. 60/348,203, filed on Oct. 26, 2001.

(51) Int. Cl.[7] .............................. A61K 9/12; A61K 9/72
(52) U.S. Cl. ........................ 424/45; 424/46; 424/78.12; 424/450; 424/488; 514/826; 514/169; 128/200.14
(58) Field of Search .................. 424/45, 46, 78.12, 424/450, 488; 514/826, 169; 128/200.14

(56) References Cited

U.S. PATENT DOCUMENTS

| | | |
|---|---|---|
| 3,644,353 A | 2/1972 | Lawrence et al. .... 260/247.5 R |
| 3,879,442 A | 4/1975 | Schwender et al. ......... 260/471 |
| 4,448,776 A | 5/1984 | Bucher et al. .............. 424/250 |
| 4,499,108 A | 2/1985 | Sequeira et al. ............ 514/653 |
| 4,751,071 A | 6/1988 | Magruder et al. .......... 424/467 |
| 4,853,381 A | 8/1989 | Finch et al. ................ 514/211 |
| 4,908,386 A | 3/1990 | Finch et al. ................ 514/605 |
| 4,939,147 A | 7/1990 | Dixon et al. ................ 514/603 |
| 5,292,499 A | 3/1994 | Evans et al. .................. 424/45 |
| 5,340,587 A | 8/1994 | Mihalko et al. ............ 424/450 |
| 5,362,755 A | 11/1994 | Barberich et al. .......... 514/649 |
| 5,393,531 A | 2/1995 | Gerhard et al. ............. 424/466 |
| 5,474,759 A | 12/1995 | Fassberg et al. .............. 424/45 |
| 5,508,023 A | 4/1996 | Byron et al. .................. 424/45 |
| 5,536,444 A | 7/1996 | Hettche et al. ............. 252/305 |
| 5,538,999 A | 7/1996 | Clark et al. ................ 514/65.3 |
| 5,603,918 A | 2/1997 | McNara ....................... 424/46 |
| 5,674,471 A | 10/1997 | Akehurst et al. ............. 424/45 |
| 5,676,930 A | 10/1997 | Jager et al. .................... 424/45 |
| 5,708,036 A | 1/1998 | Pesterfield, Jr. ............. 514/653 |
| 5,763,449 A | 6/1998 | Anaebonam et al. ....... 514/275 |
| 5,844,002 A | 12/1998 | Barberich et al. .......... 514/649 |
| 5,849,265 A | 12/1998 | Li-Bovet et al. .............. 424/45 |
| 5,902,606 A | 5/1999 | Wunderlich et al. ........ 424/464 |
| 5,919,827 A | 7/1999 | Barberich et al. .......... 514/651 |
| 5,955,058 A | 9/1999 | Jager et al. .................... 424/45 |
| 5,980,882 A | 11/1999 | Eichman .................. 424/78.12 |
| 5,981,474 A | 11/1999 | Manning et al. ................ 514/2 |
| 6,007,843 A | 12/1999 | Drizen et al. ................ 424/488 |
| 6,030,604 A | 2/2000 | Trofast ......................... 424/46 |
| 6,030,682 A | 2/2000 | Merecki ..................... 428/66.4 |
| 6,057,307 A | 5/2000 | Sequeira et al. ............ 514/169 |
| 6,083,993 A | 7/2000 | Barberich et al. .......... 514/649 |
| 6,123,924 A | 9/2000 | Mistry et al. .................. 424/45 |
| 6,136,294 A | 10/2000 | Adjei et al. .................... 424/45 |
| 6,153,173 A | 11/2000 | Sapsford et al. .............. 425/45 |
| 6,153,211 A | 11/2000 | Hubbell et al. ............. 424/426 |
| 6,165,500 A | 12/2000 | Cevc .......................... 424/450 |
| 6,221,398 B1 | 4/2001 | Jakupovic et al. .......... 424/489 |
| 6,221,887 B1 | 4/2001 | Asghar et al. .............. 514/357 |
| 6,228,346 B1 | 5/2001 | Zhang et al. ................... 424/45 |
| 6,235,725 B1 | 5/2001 | Ahmed ........................ 514/56 |
| 6,238,647 B1 | 5/2001 | Akehurst et al. ............. 424/45 |
| 6,251,368 B1 | 6/2001 | Akehurst et al. ............. 424/45 |
| 6,258,341 B1 | 7/2001 | Foster et al. ................... 424/45 |
| 6,261,539 B1 | 7/2001 | Adjei et al. .................... 424/46 |
| 6,284,287 B1 | 9/2001 | Sarlikiotis et al. .......... 424/689 |
| 6,287,540 B1 | 9/2001 | Trofast ......................... 424/46 |
| 6,294,192 B1 | 9/2001 | Patel et al. .................. 424/451 |
| 6,299,861 B1 | 10/2001 | Banholzer et al. ............ 424/45 |
| 6,451,289 B2 * | 9/2002 | Wherry, III et al. .......... 424/45 |
| 2002/0002204 A1 | 1/2002 | Wherry et al. .............. 514/653 |

FOREIGN PATENT DOCUMENTS

| | | |
|---|---|---|
| EP | 0 37 632 | 5/1990 |
| WO | WO 94 13262 | 6/1994 |

OTHER PUBLICATIONS

PDR's drug informationon Accuneb ® (Dey), Sep. 2001. (obtained from on–line PDR).*

Alderson S. H., Warren R. H.: "Pediatric Aerosol Therapy Guidelines" Indications, Techniques, and Dosages Clinical Pediatrics, vol. 23, No. 10, 1984, pp. 553–557.

Global Burden of Disease and Injury Series Volume 1 The Global Burden of Disease—A comprehensive assessment of mortality and disability from diseases, injuries, and risk factors in 1990 and projected to 2020—Christopher J.L. Murray, Harvard University, Boston, MA, USA; Alan D. Lopez, World Health Organization, Geneva, Switzerland (1996).

The Allergy Report American Academy of Allergy, Asthma & Immunology, Inc. Overview of Allegic Diseases—Diagnosis, Management, and Barriers to Care—vol. 1 Diseases of the Atopic Diathesis—vol. 2. Conditions That May Have an Allergic Component—vol. 3 (2000).

(List continued on next page.)

Primary Examiner—Michael G. Hartley
Assistant Examiner—M. Haghighatian
(74) Attorney, Agent, or Firm—Coudert Brothers LLP

(57) ABSTRACT

The present invention relates to an albuterol inhalation solution, system, kit and method for relieving bronchospasm in children suffering from asthma. In one alternative embodiment, the solution of the present invention is a sterile, premixed, premeasured single unit dose of albuterol for asthmatic patients 2 to 12 years of age. The present solution may be free of anti-microbial preservatives, such as benzalkonium chloride. In another alternative embodiment, the solution of the present invention comprises about 0.63 mg or about 1.25 mg albuterol.

9 Claims, 4 Drawing Sheets

OTHER PUBLICATIONS

A Randomized Trial to Improve Self–Management Practices of Adults With Asthma Wiliam C. Bailey, MD; James M. Richard, Jr., PhD; C. Michael Brooks, EdD; Seng–jaw Soong: PhD; Richard A. Windsor, PhD, MPH: Bryn A. Manzella, MPH—Arch Inter Med—vol. 150, Aug. 1990 Adults With Asthma—Bailey et al.

Patient error in use of bronchodilator metered aerosols British Medical Journal—Jan. 10, 1990.

National Asthma Education and Prevention Practical Guide for the Diagnosis and Management of Asthma National Institutes of Health—Nationa Heart, Lung and Blood Institute NIH Publication No. 97–4053, Oct. 1997.

Pediatric Management Problems Pediatric Nursing/May–Jun. 1994/vol. 20/No.3.

Guidelines for the Diagnosis and Management of Asthma National Institutes of Health—National Heart, Lung and Blood Association—NIH Publication–No. 97–4051—Jul. 1997.

National Institutes of Health National Heart, Lung, and Blood Insitute Data Fact Sheet—Asthma Statistics U.S. Department of Health and Human Services Jan. 1999.

Morbility & Mortality: 2000 Chart Book on Cardiovascular, Lung and Blood Diseases—National Institutes of Health National, Heart, Lung, and Blood Institute May 2000.

Xopenex™ (levalbuterol HCI) Inhalation Solution*, 0.63 mg, 1.25 mg (1992).

Ventolin® (albuterol, USP) Inhalation Aerosol Bronchodilator Aerosol For Oral Inhalation Only (2001).

JAMA Asthma Information Center—Oct. 26, 2001 Ventolin Syrup www.ama–assn–org/special/asthma/treatmnt/drug/ventolin.htm.

Summary of Product Characteristics—Ventolin Nebules (1998–06) S:\Inetpub\wwwsites\corpdev\Product pdfs\uk_ventolin _nebules.doc.

Product Information PROVENTIL®HFA http:fb.a–files.net/PackageInsert/schering/23800101.htm (1996).

Proventil® brand of albuterol sulfate, USP Inhalation Solution 0.083%*, Prescriber information. (1999).

Allergic Reactions in Children, Practical pharmacotherapy for Pediatric Asthma Douglas Barett, MD, Pediatric Annals, 29:12, Dec. 2000.

Undiluted Albuterol Aerosols in the Pediatric Emergency Department David J. Gutglass, MD*; Louis Hampers, MD, MBA*; Doreen Teoh, MD*; Sai r. Nimmagadda, MD; and Steven E. King, MD, Pediatric, 105:5, May 2000 www.pediatrics.org./cgi/content/full/105/5e67.

Efficacy of Albuterol in the Management of Bronchiolitis Anne M. Gadomski, MD: MPH; Richard Lichenstein, MD; Lisa Horton, MD, James King, MD; Virginia Keane, MD; and Thomas Permutt, PhD, Pediatrics, 93:6, Jun. 1994.

A prospective, randomized study of continous versus intermittent nebulized albuterol for severe status asthmaticus in children Michele C. Papo, MD, MPD; John Frank; RRT' Ann E. Thompson, MD, FCCM, Critical Care Medicine, 21:10, Oct. 1993.

Randomized controlled trial of ipratropium bromide and frequent low doses of salbutamol in the management of mile and moderate acute pediatric asthma Francine M. ducharme, MD and G. Michael Davis, MD The Journal of Peidatrics—Oct. 1998.

Continuous Nebulization: A Treatment Modality For Pediatric Asthma Patients. Sharon Ferrante, Eileen Painter Pediatric Nursing/July/Aug 1995/vol.21/No.4.

The Clinical Efficacy of Nebulized Racemis Epinephrine and Albuterol in Acute Broncholitis Tiina Reijonen, MD; Matti Korppi, MD; Sirpa Pitkakangas, MD; Sirpoa Tenhola, MD; Kyllikki Remes, MD Arch Pediatr Adolesc Med/vol. 149, Jun. 1995.

Low Dose B–Agonist Continuous Nebulization Therapy for Status Asthmaticus in Children Vicki L. Montogmery, MD, and Nemur S. Eid, MD Journal of Asthma, 31(3), 201–207 (1994).

Safety of Continuous Nebulized Albuterol for Bronchospasm in Infants and Children Robert W. Katz, MD; H. William Kelly, PharmD; Mark R. Crowley, MD; Roni Grad, MD; Bennie C. McWilliams, MD and Shirley J. Murphy, MD Demographic Characteristics of Patients Pediatrics vol. 92 No. 5 Nov. 1993.

Nebulized Albuterol in Acute Childhood Asthma: Comparison of Two Doses Suzanne Schuh, MD, FRCP(C); Michael J. Reider, MD<FRCP(C); Gerlad Canny, MBChB, FRCP(C); Emily Pender, MD; Thomas Forbes; Yok K. Tan, PHhD; David Bailey; PhD; and Henry Levision, MD, FRCP(C) Pediatrics vol. 86 No. 4 Oct. 1990.

Frequent administration by inhalation of salbutamol and ipratropium bromide in the initial management of severe acute asthma in children Joe Reiman, MD, Michele Galdes–Sebalt, MD, Farouk Kazim, MA, Gerard Canny MD and Henry Levision, MD Toronto, Ontario, Cancad—J. Allergy Clin. Immunol—Jan. 1988.

Pediatric Pharmacology and Therapeutics—Clinical and Laboratory observations Combined salbutamol and ipratropium bromide by inhalation in the treatment of severe acute asthma Raphael Beck, MD, Colin Robertson, MD, Michele Galdes–Sebaldt, MD, and Henry Levison, MD The Journal of Pediatrics—vol. 107, No. 4, Oct. 1985.

Bronchodilator Responsiveness in Normal Infants and Young Children Amy B. Goldstein, Robert G. Castile, Stephanie D. Davis, David A. Filbrun, Robert L. Flucke, Karen s. McCoy, and Robert S. Teppe Am J. Respir Crit Care Med vol. 164, pp. 447–454, 2001.

Experience with a Metered–Dose Inhaler with a Spacer in the Pediatric Emergency Department Grey Benton, RRT, MA; Randolph C. Thomas, MD; Bruce G. Nickerson, MD; John C. McQuity, MD; Jerry Okikawa, RRT, MBA AJDC–vol. 143, Jun. 1989.

Safety of Bronchodilator Therapy in Pediatic Asthma Patients—Jay E. Selcow, MD Department of Pediarics, Hartford Hospital, Harford, and University of Connecticut School of Medicime, Farmington, Connecticut Clinical Therapeutics/vol. 16, No. 4, 1994.

Delivery of Aerosol Therapy in the Management of Pulmonary Disorder Drug Topics—Sep. 2000.

Abstract: Preservatives in Nebulizer Solutions: Risk without Benefit Richard Beasley; MD, David Fishwick, MD, Jon F. Miles, MD and Leslie Hendeles, PharmD www.accp.com/pharmacotherpy/Abs 18_1/130.htm (1998).

Survey of the clinical use of pressurized aerosol inhalers S.W. Epstein, MD; C.P.R. Manning, ONCMLT; M.J. Ashley, MD, DPH, M. Sc; P.N. Corey, PhD CMA Journal/Apr. 7, 1979/vol. 120.

Patient Assessment of Efficacy of Nebulizer Systems on their Respiratory Health Survey Results—Apr. 1995, Safian Communications.

* cited by examiner

FIGURE 7

(Albuterol sulfate)
Inhalation Solution
1.25 mg*3 mL and 0.63 mg*3 mL
(*Potency expressed as albuterol, equivalent to 1.5 mg and 0.75 mg albuterol sulfate)

PATIENT'S INSTRUCTIONS FOR USE
Read this patient information completely every time your prescription is filled as information may have changed. Keep these instructions with your medication, as you may want to read them again.

The inhalation should only be used under the direction of a physician. Your physician and pharmacist have more information about the solution and the condition for which it has been prescribed. Contact them if you have additional questions.

Storing your medicine
Store the inhalation solution between 2 and 25 C (36 and 77 F). Vials should be protected from light before use, therefore, keep unused vials in a foil pouch.

Dose
The inhalation solution is supplied as single-dose, ready-to-use vial containing 3 mL of solution. No mixing or dilution is needed. Use one new vial with each nebulizer treatment.
Instructions for Use
1. Remove one vial form the foil pouch. Place remaining vials back into foil pouch for storage.
2. Twist the cap completely off the vial and squeeze the content into the nebulizer reservoir (Figure).

3. Connect the nebulizer to the mouthpiece or face mask (Figure 2).

4. Connect the nebulizer to the compressor.

5. Sit in a comfortable, upright position; place the mouthpiece in your mouth (figure 3) or put on the face mask (Figure 4); and turn on the compressor.

6. Breathe as calmly, deeply and evenly as possible through your mouth until no more mist is formed in the nebulizer chamber (about 5-15 minutes). At his point, the treatment is finished.

7. Clean the nebulizer

DOSAGE AND ADMINISTRATION
The usual starting dosage for patients 2 to 12 years of age is 1.25 mg or 0.63 mg of albuterol administered 3 or 4 ties daily, as needed, by nebulization. More frequent administration is not recommended. To administer 1.25 mg or 0.63 mg albuterol, use the entire contents of the one unit-dose vial (3 mL of 1.25 mg or 0.63 mg inhalation solution by nebulization). Adjust nebulizer flow rate to deliver solution over 5 to 15 minutes.

The use of the inhalation solution can be continued as medically indicated to control recurring bouts of bronchospasm. During this time most patients gain optimum benefit for regular use of the inhalation solution.

Patients 6 to 12 year of age with more sever asthma (baseline FEV1 less than 60% predicted), weight >40kg, or patients 11 to 12 years of age may achieve a better initial response with the 1.25 mg dose.

HOW SUPPLIED

The albuterol sulfate inhalation solution is supplied as a 3mL., clear, colorless, sterile, preservative-free, aqueous solution in two different strengths. 0.63 mg and 1.25, of albuterol (equivalent to 0.75 mg of albuterol sulfate or 1.5 mg of albuterol sulfate per 3 mL) in uint-dose low-density polyethylene (LDPE)vials. Each unit-dose LDPE vial is protected in a foil-pouch, and each foil pouch contains 5 unite-dose LDPE vials. Each strength of AccuNeb (albuterol sulfate) inhalation solution is available in a shelf carton containing multiple foil pouches.

(albuterol sulfate) Inhalation Solution, 0.63 mg (potency expressed as albuterol) contains 0.75 mg albuterol sulfate per 3 mL in unit-dose vial and is available in the following packaging configuration.

5 foil pouches, each containing 5 vials, total 25 vials per carton

(albuterol sulfate) Inhalation Solution, 1.25 mg (potency expressed as albuterol) contains 1.50 mg albuterol sulfate per 3 mL in unit-dose vial and is available in the following packaging configuration.

5 foil pouches, each containing 5 vials, total 25 vials per carton

STORAGE

Store between 2°C and 25°C (36°F and 77°F) Protect from light and excessive heat.

Store unit-dose vials in protective foil pouch.

ALBUTEROL INHALATION SOLUTION, SYSTEM, KIT AND METHOD FOR RELIEVING SYMPTOMS OF PEDIATRIC ASTHMA

I. CROSS REFERENCE TO RELATED APPLICATIONS

This application claims priority under 35 U.S.C. §119 from U.S. Provisional Application Ser. No. 60/348,203 filed Oct. 26, 2001, which is incorporated herein by reference in its entirety.

II. FIELD OF THE INVENTION

The present invention relates to an albuterol inhalation solution, system, kit and method for relieving symptoms associated with asthma in children.

III. BACKGROUND OF INVENTION

Asthma is a pulmonary disease marked by (1) labored breathing; (2) wheezing; and (3) coughing. Asthma is characterized by: (1) airway inflammation; (2) airway hyperresponsiveness; and (3) airway obstruction (or airway narrowing) that is partially or completely reversible, either spontaneously or with treatment. Common symptoms of asthma include wheezing, shortness of breath, tightness in the chest and a persistent cough. The severity of the symptoms vary widely from patient to patient, and even from one episode (attack) to the next.

A key condition of asthma is chronic inflammation of the linings of the lungs. This inflammation is associated with an increase in airway sensitivity (hyperresponsiveness) to stimuli such as allergens, irritants, cold air and viruses. When exposed to these triggers, the linings undergo an allergic reaction, causing spasms that constrict the airways. This bronchoconstriction, in combination with edema and the release of thickened secretions, reduces movement of air through the lungs, resulting in the symptoms commonly associated with asthma.

Asthma is the most common chronic lung disease in children. Asthma prevalence in children has reportedly increased in the United States by 160%. Asthma hospitalization rates are also higher in young children due, in part, to difficulties in using currently available drug delivery devices and failure to use optimal doses of asthma therapies.

Despite progress in emergency and critical care medicine, the pediatric mortality rate from asthma ranges from 0.2 to 0.4 per 100,00 population, depending on age. Pediatric asthma ranks as the $7^{th}$ leading cause of death among children ages 10 to 14 years. Approximately 0.05% of known children with asthma die annually from the disease.

Short-acting inhaled beta-agonists, such as albuterol, are the first choice treatment for relieving symptoms of acute asthma in children. Albuterol is currently available as a 2.5 mg unit dose (0.083%) inhalation solution for use in nebulizers. Although this dose has been approved for use by adults, the FDA has recently expanded labeling guidelines to include this amount of albuterol for use by pediatric asthmatic patients as young as 2 years old. However, when administered on a regular basis to a child, the 2.5 mg formulation may provide more albuterol than needed, thereby increasing the risk of adverse drug effects.

In the recently revised guidelines for asthma treatment, the National Institutes of Health recommended that pediatric patients use the lowest beta-agonist doses needed to control symptoms. However, using lower doses of albuterol in patients under age 12 to reduce the risk of side effects necessitates dilution of currently available asthma medications. This poses several problems because parents, care givers, teachers and others typically do not have adequate experience diluting these medications, resulting in contamination or inappropriate dosing, among other problems.

Also, antimicrobial preservatives, such as benzalkonium chloride (BAC), are often present in inhalation solutions used to treat asthma and chronic obstructive pulmonary disease (COPD). The presence of BAC in these solutions generally does not affect the short-term (single dose) bronchodilator response. However, case reports suggest that repeated use of asthma treatments with BAC may result in paradoxic bronchoconstriction. When inhaled by asthmatic subjects, BAC may also cause dose-dependent bronchoconstriction. Despite these side effects, many commercially available albuterol inhalation solutions contain BAC.

There is, therefore, a need for an improved albuterol inhalation solution, system, kit and method for relieving symptoms associated with pediatric asthma.

IV. SUMMARY OF THE INVENTION

One object of the present invention is to provide an albuterol inhalation solution for the relief of bronchospasm in children with asthma. Another object of the present invention is to provide a prepackaged, sterile, premixed, premeasured, reduced-dosage albuterol inhalation solution for the relief of bronchospasm in patients 2 to 12 years of age with asthma.

It is yet another object of the present invention to provide an antimicrobial preservative-free albuterol inhalation solution to relieve bronchospasm in a pediatric patient with asthma.

A further object of the present invention is to provide a method of administering an albuterol inhalation formulation for relief of bronchospasm associated with pediatric asthma.

An additional object of the present invention is to provide a kit or system for relief of bronchospasm in a pediatric patient with asthma.

A further object of the present invention is to provide a process for making an inhalation solution for relief of bronchospasm in a pediatric patient with asthma.

Another object of the invention includes a device for use in relieving bronchospasm in a pediatric patient with asthma.

Other objects, features and advantages of the present invention will be apparent to those of ordinary skill in the art in view of the following detailed description of the invention and accompanying drawings.

V. BRIEF DESCRIPTION OF THE DRAWINGS

FIG. 7 depicts a non-limiting example of a label utilized in the present invention.

VI. DETAILED DESCRIPTION OF THE INVENTION

Albuterol

Figure 1:
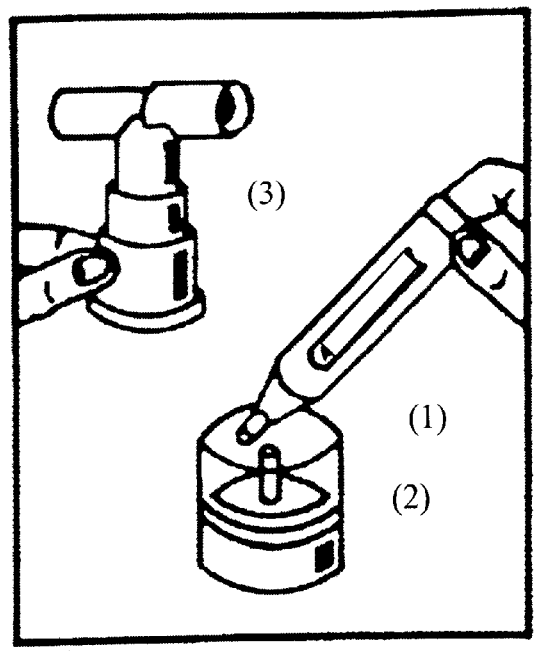
FIGS. 1–4 depict a non-limiting example of administering the inhalation solution of the present invention by a nebulizer.
Figure 2:
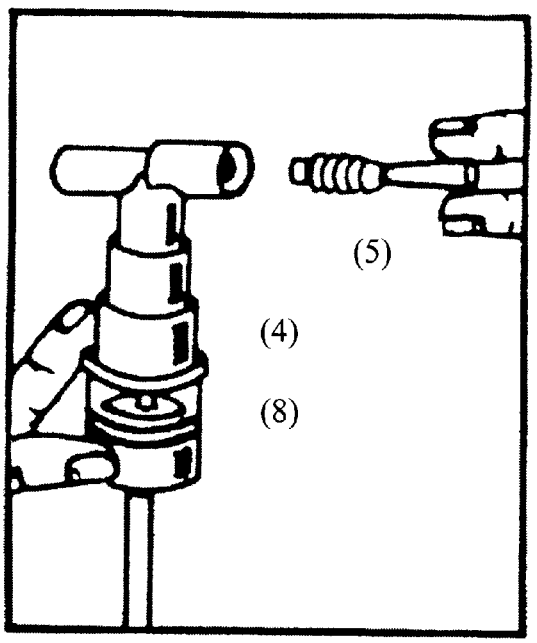

The present invention relies on the bronchodilation effects of albuterol to provide relief from symptoms associated with pediatric asthma. As used herein, the term "albuterol" includes, but is not limited to, any form of albuterol which is capable of producing a desired bronchodilation effect in pediatric patients, including, but not limited to, all tautomeric forms, enantomeric forms, stereoisomers, anhydrides, acid addition salts, base salts, solvates, analogues and derivatives of albuterol.

In the present invention, acceptable salts of albuterol may include, but are not limited to, hydrochloride, sulfate, maleate, tartrate, citrate and the like. These and other acceptable salts are described in U.S. Pat. No. 3,644,353, which is incorporated herein by reference in its entirety.

In the present invention, the preferred salt of albuterol is sulfate. In an alternative embodiment, the inhalation solution of the present invention comprises the sulfate salt of racemic albuterol. Albuterol sulfate is a relatively selective beta-2-adrenergic bronchodilator with an empirical formula of $C_{13}H_{21}NO_3$. The chemical name for albuterol sulfate is $\alpha^1$-[(tert-butylamino)methyl]-4-hydroxy-m-xylene-$\alpha$, $\alpha'$-diol sulfate (2:1)(salt), and its established chemical structure is as follows:

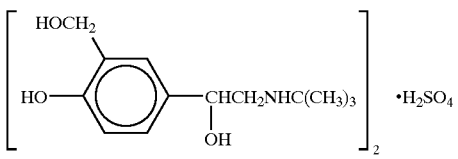

In the present invention, the albuterol may be provided in a variety of pharmaceutically acceptable vehicles, including, but not limited to, water or other aqueous solutions comprising a pharmaceutically acceptable amount of an osmotic agent.

In one alternative embodiment, the inhalation solution of the present invention comprises a therapeutically effective pediatric amount of albuterol. As used herein the phrase "therapeutically effective pediatric amount of albuterol" means a safe and tolerable amount of albuterol for pediatric patients, as based on industry and/or regulatory standards. Such amount being sufficient to effectively induce bronchodilation and/or provide relief of bronchospasm in children.

In the inhalation solution of the present invention, a therapeutically effective pediatric amount of albuterol may include about 0.63 mg or about 1.25 mg albuterol. Here, the potency of the albuterol is equivalent to about 0.75 mg and about 1.50 mg of albuterol sulfate, respectively. In an alternative embodiment, a therapeutically effective pediatric amount of albuterol may include from about 0.63 mg to about 1.25 mg of albuterol. In another alternative embodiment, such pediatric amount comprises no more than about 1.25 mg of albuterol, or it comprises 1.25 mg of albuterol or less.

In another alternative embodiment of the present invention, a therapeutically effective pediatric amount of albuterol may include from about 0.08 mg to about 1.90 mg albuterol, including the following intermediate amounts of albuterol: about 0.08 mg to about 0.20 mg; about 0.21 mg to about 0.50 mg; about 0.51 mg to about 0.60 mg; about 0.61 mg to about 0.70 mg; about 0.71 mg to about 0.80 mg; about 0.81 mg to about 0.90 mg; about 0.91 mg to about 1.0 mg; about 1.01 mg to about 1.05 mg; about 1.06 mg to about 1.10 mg; about 1.11 mg to about 1.15 mg; about 1.16 mg to about 1.20 mg; about 1.21 mg to about 1.25 mg; about 1.26 mg to about 1.30 mg; about 1.31 mg to about 1.35 mg; about 1.36 mg to about 1.40 mg; about 1.41 mg to about 1.45 mg; about 1.46 mg to about 1.50 mg; about 1.51 mg to about 1.55 mg; about 1.56 mg to about 1.60 mg; about 1.61 mg to about 1.65 mg; about 1.66 mg to about 1.70 mg; about 1.71 mg to about 1.75 mg; about 1.76 mg to about 1.80 mg; about 1.81 mg to about 1.85 mg; about 1.86 mg to about 1.90 mg.

In another alternative embodiment of the present invention, a therapeutically effective pediatric amount of albuterol may include from about 0.1 mg to about 2.5 mg albuterol sulfate, including the following intermediate amounts of albuterol sulfate: about 0.1 mg to about 0.2 mg; about 0.3 mg to about 0.4 mg; about 0.5 mg to about 0.6 mg; about 0.7 mg to about 0.8 mg; about 0.9 mg to about 1.00 mg; about 1.01 mg to about 1.20 mg; about 1.21 mg to about 1.40 mg; about 1.41 mg to about 1.60 mg; about 1.61 mg to about 1.80 mg; about 1.81 mg to about 2.00 mg; about 2.01 mg to about 2.20 mg; about 2.21 mg to about 2.40 mg; about 2.41 mg to about 2.50 mg.

In another alternative embodiment of the present invention, a therapeutically effective pediatric amount of albuterol may include from about 0.002% to about 0.075% by weight albuterol, including the following intermediate amounts of albuterol: about 0.002 wt % to about 0.010 wt %; about 0.011 wt % to about 0.020 wt %; about 0.021 wt % to about 0.030 wt %; about 0.031 wt % to about 0.040 wt %; about 0.041 wt % to about 0.050 wt %; about 0.051 wt % to about 0.060 wt %; about 0.061 wt % to about 0.070 wt %; about 0.071 wt % to about 0.075 wt %.

In another alternative embodiment of the present invention, a therapeutically effective pediatric amount of albuterol may include from about 0.003% to about 0.1% by weight albuterol sulfate in solution, including the following intermediate amounts of albuterol sulfate: about 0.003 wt % to about 0.010 wt %; about 0.011 wt % to about 0.020 wt %; about 0.021 wt % to about 0.030 wt %; about 0.031 wt % to about 0.040 wt %; about 0.041 wt % to about 0.050 wt %; about 0.051 wt % to about 0.060 wt %; about 0.061 wt % to about 0.070 wt %; about 0.071 wt % to about 0.080 wt %; about 0.081 wt % to about 0.090 wt %; about 0.091 wt % to about 0.10 wt %.

Most pharmaceutical inhalation solutions contain an antimicrobial preservative such as BAC or EDTA. One problem with BAC-containing solutions is that the BAC may cause paradoxic bronchoconstriction if the solution is administered repeatedly over short intervals. Another problem is that, when inhaled by asthmatic patients, the BAC can cause dose-dependent bronchoconstriction. The inhalation solution of the present invention may be provided without BAC, thereby making it more suitable for pediatric patents, especially in an emergency situation where the inhalation solution is administered repeatedly over a short period of time. Also, administering a BAC-free inhalation solution to a pediatric patient reduces the concomitant liability of adverse effects associated with BAC. It also reduces the toxicity and other side effects associated with BAC.

The inhalation solution of the present invention may also be provided in sterile, unit dose treatments, thus eliminating the need to include BAC in the solution. Moreover, as shown in Table 1, in its sterile form the formulation of the present invention (which comprises a therapeutically effective pediatric amount of albuterol) provides a stable pediatric inhalation solution such that the formulation can be stored (e.g., on a shelf) for long periods of time.

TABLE 1

Stability Data

| | | 0.021 wt % Albuterol | | | 0.042 wt % Albuterol | |
|---|---|---|---|---|---|---|
| | Assay* | pH | Osmolality (mOsm/kg) | Assay* | pH | Osmolality (mOsm/kg) |
| Time zero | 98 | 3.5 | 289 | 100 | 3.5 | 291 |
| 25° C./35% RH  12 months | 99 | 3.5 | 289 | 100 | 3.5 | 291 |
| 24 months | 101 | 3.5 | 294 | 100 | 3.5 | 292 |
| 40° C./15% RH  3 months | 99 | 3.6 | 290 | 100 | 3.6 | 291 |
| 6.5 months | 96 | 3.5 | 290 | 99 | 3.5 | 292 |

*as percent of label claim (0.021 wt % and 0.042 wt % albuterol, respectively).

Another benefit of a sterile inhalation solution is that it reduces the possibility of introducing contaminants into the patient when administered, thereby reducing the chance of an opportunistic infection in the patient.

Adherence to asthma medication therapy and prevention of asthma medication error are considerable problems. These problems can be significantly reduced by providing asthmatic patients a prepackaged, premixed, premeasured amount of albuterol. Providing albuterol in this fashion makes asthma therapy simple because it increases convenience and eliminates confusion in preparing appropriate dosages. These advantages are especially significant in the treatment of pediatric asthma, where treatments often come in multiple dosage units and must be diluted to specific concentrations suitable for treating a pediatric patient. This poses several problems. For instance, asthma treatments requiring administration of a single dose unit from multiple dosage units sometimes lack proper mixing or diluting instructions, or the instructions for preparing and using the asthma treatment may be hard to follow or can be easily lost. Of even greater importance is haphazard diluting or mixing of asthma medications, which can result in administering the wrong dosage. This could be especially harmful for pediatric patients, who often are less tolerant to higher dosages of albuterol. Incorrect mixing can also result in treatment failure such that additional medical attention is required, thereby increasing the time, expense, and personnel costs associated with therapy.

The present invention overcomes the aforementioned problems by providing therapeutically effective pediatric amounts of albuterol in prepackaged, premixed, premeasured and/or unit dose amounts. In one embodiment, the present invention comprises one or more prefilled containers. The one or more containers each comprising a single unit dose of an aqueous solution comprising a therapeutically effective pediatric amount of albuterol for the relief of bronchospasm associated with pediatric asthma. Providing the inhalation solution in such a manner eliminates the need to dilute or mix asthma medications to obtain proper dosages for treatment. Also, no special pharmacy compounding is required, and the chance of medication errors are reduced. Further, there is a lower risk of cross-contamination, and less waste of medication when providing an inhalation solution in a premixed, ready to use form.

Other features of the present invention include improved user compliance and quality of life as compared to conventional treatments for relieving bronchospasm in children. While the level of compliance of any asthma treatment depends in part on the motivation and skill of the individual dispensing the treatment, compliance nevertheless may be improved by controllable factors such as the ease with which the treatment may be administered, as well as the desirability of receiving the treatment.

The present invention provides a convenient, fast and reliable treatment for relieving bronchospasm in children, and clearly represents an improvement over traditional asthma treatments. Also, the present invention is designed to facilitate user compliance by providing one or more dispensing containers comprising a premixed, premeasured inhalation solution comprising a single unit dose of a therapeutically effective pediatric amount of albuterol for the relief of bronchospasm in children. Said containers may be utilized in a method of relieving such bronchospasm, or the containers may be incorporated in a system and/or kit for treating the same.

In one alternative embodiment, the formulation of the present invention is a sterile, premixed, premeasured, BAC-free inhalation solution comprising a single unit dose of a therapeutically effective pediatric amount of albuterol in a single container. Each unit dose container comprises either 0.75 mg/3 ml of albuterol sulfate (equivalent to 0.63 mg of albuterol) or 1.50 mg/3 ml of albuterol sulfate (equivalent to 1.25 mg of albuterol) in a sterile, aqueous solution. Sodium chloride may be added to adjust the isotonicity of the solution and sulfuric acid may be added to adjust pH of the solution to about 3.5. The inhalation solution of the present invention may or may not include a chelating agent, such as EDTA.

In another alternative embodiment, the inhalation solution of the present invention may be supplied as a 3 ml, sterile, BAC-free, nebulizer solution comprising from about 0.75 mg/3 ml to about 1.50 mg/3 ml of albuterol sulfate (equivalent to about 0.63 mg to about 1.25 mg of albuterol, respectively). The nebulizer solution is contained in a unit-dose, low-density polyethylene (LDPE) container. Each unit-dose container may be disposed in a foil pouch, and each foil pouch may contain 5 or more unit-dose containers. Each foil pouch containing the unit dose container may be disposed in a shelf carton.

The present invention provides an albuterol inhalation solution for relieving bronchospasm in a pediatric patient with asthma, including, but not limited to, allergic (extrinsic) asthma, non-allergic (intrinsic) asthma, occupational asthma and aspirin sensitive asthma. The present invention also provides an albuterol inhalation solution for relieving bronchospasm associated with different classes of pediatric asthma including, but not limited to, severe persistent asthma, moderate persistent asthma, mild persistent asthma and mild intermittent asthma. Some characteristics associated with the different classes of asthma are shown in Table 2. The information in this table is presented for illustrative purposes only. It is not intended to limit the scope of the invention.

TABLE 2

| Type of Asthma | Description |
| --- | --- |
| Severe Persistent | Continual symptoms during the day; Frequent symptoms at night; 60% of lower predicted values for DEV; and >60% or lower of personal best PEF, and more than 30% PEF variability. |
| Moderate Persistent | Some symptoms every day; Nighttime symptoms five or more nights a month; and >60% and <80% of PEF or $FEV_1$ and greater than 30% $FEV_1$ variability. |
| Mild Persistent | Daytime symptoms 3–6 days a week; Symptoms at night 3–4 times a month; and 80% or higher PEF or $FEV_1$ and PEF variability of 20–30%. |
| Mild Intermittent | Daytime symptoms 2 or fewer times a week; Nighttime symptoms 2 or fewer times a month; and 80% or higher PEF or $FEV_1$ and PEF variability <20%. |

In the present invention, a therapeutically effective pediatric amount of albuterol is administered to induce bronchodilation and/or provide relief of bronchospasm in pediatric patients with asthma. Such amount of albuterol may be administered to a pediatric patient after the onset of bronchospasm to reduce breathing difficulties resulting from asthma. In another embodiment, the albuterol may be administered prophylactically, that is, to prevent or to reduce the extent of bronchospasm.

The quantity of albuterol to be administered will be determined on an individual basis, and will be based at least in part on consideration of the patient's size, the severity of the symptoms to be treated and the results sought. The actual dosage (quantity of albuterol administered at a time) and the number of administrations per day will depend on the mode of administration, such as inhaler, nebulizer or oral administration. For example, about 0.63 mg to about 1.25 mg of albuterol given by nebulization one or more times per day would be adequate to produce the desired bronchodilation effect in most children.

In an alternative embodiment, the inhalation solution of the present invention provides relief of bronchospasm in patients 2 to 12 years of age. For example, a 0.63 mg unit dose of albuterol inhalation solution is effective for children ages 10 years and younger, children weighing ≦40 kg or children with less severe asthma. A 1.25 mg unit dose of albuterol is effective for prolonged use in children ages 11–12 years, children weighing >40 kg or in children with more severe asthma.

Further, the albuterol inhalation solution of the present invention may be administered together with one or more other drugs. For example, an antiasthmatic drug such as theophylline or terbutaline, or an antihistamine or analgesic such as aspirin, acetaminophen or ibuprofen, may be administered with or in dose temporal proximity to administration of a therapeutically effective pediatric amount of albuterol. The albuterol and the one or more drugs may be administered in one formulation or as two separate entities. According to the present invention, a therapeutically effective pediatric amount of albuterol, alone or in combination with another drug(s), may be administered to a pediatric individual periodically as necessary to reduce symptoms of asthma.

In an alternative embodiment of the present invention, relief of severe persistent asthma may include administration of a therapeutically effective pediatric amount of albuterol for quick relief of symptoms and a high dose of inhaled corticosteroids using a spacer or holding chamber with a face mask. If needed, oral corticosteroids (2 mg/kg/day) may be administered. Oral corticosteroid should be reduced to the lowest daily or alternate-day dose that stabilizes symptoms.

For moderate persistent asthma, treatment may include administering therapeutically effective pediatric amounts of albuterol for quick relief of symptoms and an inhaled corticosteroid at a mid-level dose, delivered using a spacer or holding chamber with a facemask. As symptom control is achieved, the inhaled corticosteroid dose may be lowered, and either inhaled nedocromil or theophylline may be added.

For mild persistent asthma, treatment may include administering therapeutically effective pediatric amount(s) of the present formulation for quick relief of symptoms and daily anti-inflammatory medication such as low-dose inhaled corticosteroid using a spacer or holding chamber with a facemask or a trial of cromolyn by nebulizer or nedocromily by MDI. For mild intermittent asthma, aside from administering a therapeutically effective pediatric amount of albuterol, no daily drug therapy is ordinarily required.

In another alternative embodiment, the inhalation solution of the present invention may be administered by nebulizer, such nebulizer including, but not limited to, a jet nebulizer, ultrasonic nebulizer and breath-actuated nebulizer. Preferably, the nebulizer is a jet nebulizer connected to an air compressor with adequate air flow. The nebulizer being equipped with a mouthpiece or suitable face mask.

In an alternative embodiment, the system and/or kit of the present invention comprises an inhalation solution comprising a therapeutically effective pediatric amount of albuterol in a prepackaged, premeasured, premixed and/or single unit dose form for the relief of bronchospasm in children. The inhalation solution may be sterile and/or antimicrobial preservative-free.

In another embodiment, the present invention provides a system and/or kit for organizing and storing one or more prefilled dispensing containers, each container comprising a premixed, premeasured inhalation solution comprising a single unit dose of a therapeutically effective pediatric amount of albuterol. Such system and/or kit may provide such containers in prepackaged form. The one or more containers may be comprised of plastic including, but not limited to, a semi-permeable plastic such as, for example, LDPE. The container may also comprise a Twist-Flex™ top, such top comprising an easy-to-grip tab-like handle such that the container may be opened, for example, by twisting off the tab by hand. The Twist-Flex™ top is advantageous in that it allows for easy dispensing of the solution, prevents spillage and eliminates the need to open the container by cutting off the top, or the like, thereby reducing cross-contamination. One or more of the semi-permeable single unit dose containers may be disposed in a sealed aluminum foil pouch, such that the foil provides a protective barrier against environmental contaminants and light. Such a barrier improves the shelf-life and stability of the inhalation solution.

In another alternative embodiment, the present invention comprises a prepackaged inhalation system and/or kit suitable for pediatric patients suffering from asthma. Such prepackaged system and/or kit comprising: (a) one or more single unit dosages of a therapeutically effective pediatric amount of albuterol; (b) administration instructions for the use of said unit dose as an asthma treatment for pediatrics; and (c) a dispensing container prefilled with the one or more single unit doses of albuterol.

In another alternative embodiment, the prepackaged inhalation system and/or kit of the present invention provides one or more premixed, premeasured, single unit dose vials comprising a therapeutically effective pediatric amount of albuterol for the relief of bronchospasm associated with pediatric asthma, and instructions for using the same.

Figure 5:
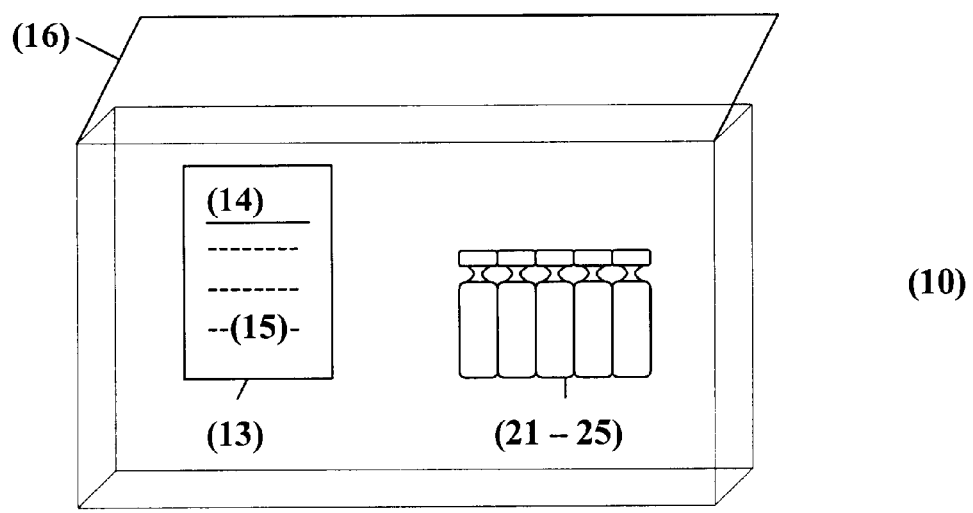
FIG. 5 depicts a non-limiting example of a unified prepackaged kit or system of the present invention.

The prepackaged inhalation system and/or kit may be provided in one of any number of forms, including, but not limited to, a box containing one or more prepackaged, unit dose vials or a box containing individual packages or pouches comprising one or more unit dose vials. For example, an embodiment of a unified prepackaged system and/or kit for relieving bronchospasm in children is depicted in FIG. 5. Specifically, FIG. 5 depicts a support package, box, carton or container (10) comprising one or more prepackaged, pre-filled dispensing containers (21–25). Each container comprising a premixed, premeasured inhalation solution. The inhalation solution comprising a unit dose of a therapeutically effective pediatric amount of albuterol for relieving bronchospasm in a child suffering from asthma. The inhalation solution may be provided in sterile and/or antimicrobial preservative-free form.

Support package, box, carton or container (10) may incorporate one or more labels (13) therein. One or more labels (13) may comprise indicia (14) indicating that the inhalation solution can be used to relieve bronchospasm in children. The label may also comprise indicia (15) which provides instructions for using the inhalation solution to relieve bronchospasm in children. As used herein "indicia" includes, but is not limited to, wording, pictures, drawings, symbols and/or shapes. A non-limiting example of the indicia that may appear on the one or more labels (13) is shown in FIG. 7. The one or more labels may be positioned on one or more surfaces of the support package, box, carton or container (10) or a separate sheet, or any combination thereof. Support package (10) may also incorporate lid (16) to enclose the packaging material therein.

The system and/or kit of the present invention may also include a label and/or instructions designed to facilitate user compliance. For example, in an embodiment, a system and/or kit of the present invention comprises packaging material containing one or more prepackaged vials comprising a sterile, premixed, premeasured, unit dose of an inhalation solution comprising a therapeutic effective pediatric amount of albuterol. The packaging material may further comprise a label indicating that each vial can be used with each nebulizer treatment for the relief of bronchospasm associated with pediatric asthma. Such instructions may also include instructions on dosage for each nebulizer treatment, as well as instructions for administration, such as by nebulizer. The instructions may be positioned on one or more surfaces of the packaging material, or the instructions may be provided on a separate sheet, or any combination thereof.

The present invention is also directed to a method of treating bronchospasm associated with pediatric asthma, wherein albuterol is administered as a unit dose from about 0.63 mg to about 1.25 mg of albuterol. Such unit dose may be in the form of a nebulizer solution.

In an alternative embodiment, the method of the present invention comprises the step of administering to a patient 2 to 12 years old in need thereof an inhalation solution comprising a therapeutically effective pediatric amount of albuterol. Such solution may comprise from about 0.63 mg to about 1.25 mg albuterol. Such solution may also be premixed, premeasured, antimicrobial preservative-free and/or sterile. Such solution may also be in a single unit dose vial.

In another alternative embodiment, the method of the present invention comprises the step of administering to a pediatric patient in need thereof an inhalation solution comprising a therapeutically effective pediatric amount of albuterol. The inhalation solution being administered by nebulizer, more preferably a jet nebulizer connected to an air compressor with adequate air flow.

In yet another alternative embodiment, in reference to FIGS. 1–4, the method of the present invention comprises the steps: (i) placing an inhalation solution comprising a therapeutically effective pediatric amount of albuterol (1) into a nebulizer cup (2) the nebulizer may be powered by attachment to compressed gas cylinders or an electrically driven compressor; (ii) using a "T" adapter (3) to fit the cup lid (4) to a mouthpiece (5) or facemask (6); (iii) drawing the albuterol solution up by the velocity of a gas jet and fragmenting it into an aerosol; (iv) passing the aerosol through the mouthpiece (5) or facemask (6) to the pediatric patient (7) afflicted with bronchospasm; and (v) the patient continues breathing until no more mist is formed in the nebulizer chamber (8). This may occur in about 5–15 minutes.

In one alternative embodiment, the usual starting dosage for patients 2 to 12 years of age is about 1.25 mg or about 0.63 mg of albuterol administered 3 or 4 times daily, as needed by nebulization. To administer these amounts of albuterol, the entire contents of a one unit-dose vial (e.g., 1.50 mg/3 ml or 0.75 mg/3 ml albuterol sulfate) may be used by nebulization. Preferably, the nebulizer flow rate is adjusted to deliver the albuterol sulfate over 5 to 15 minutes. Patients 6 to 12 years of age with more severe asthma (baseline $FEV_1$ less than 60% predicated), weight >40 kg or patients 11 to 12 years of age may achieve a better initial response with about a 1.25 mg dose.

Further, in an alternative embodiment, the method of the present invention comprises the steps: (i) preparing an inhalation solution comprising a therapeutically effective pediatric amount of albuterol solution by diluting one or more solutions comprising albuterol; and (ii) administering the inhalation solution to a pediatric patient in need thereof.

The present invention also provides a process for making a sterile, premixed, premeasured, and/or BAC-free inhalation solution comprising a single unit dose of a therapeutically effective pediatric amount of albuterol. In such an embodiment, the method of the present invention comprises one or more of the following steps: (i) adding at least a therapeutically effective pediatric amount of albuterol in a vehicle, such as water; (ii) optionally sterilizing the solution and sealing the container. An osmotic adjusting agent may be added to adjust the isotonicity of the solution. In one embodiment of the present invention, the solution of the present invention is isotonic. Isotonicity may be achieved by adding an osmotic adjusting agent to adjust the isotonicity of the solution from about 280 to about 320 mOsm/kg. In addition, an acid (e.g., sulfuric acid) may be added to adjust the pH of the solution to a level ranging from about 3.0 to about 4.0, preferably about 3.5.

In another embodiment, a process for making an inhalation solution of the present invention comprises one or more of the following steps: (i) adding at least a therapeutically effective pediatric amount of albuterol in a vehicle such as water; (ii) placing the mixture in a container, and sterilizing the mixture by steam sterilization, or any other sterilizing means known in the art. Each mixture being filled into a vial, and then packaged, stored and/or used directly. Here, the resulting mixture is stable, and after sterilization, it can be dispersed, if necessary, into multiple mixtures each containing a unit dose of a therapeutically effective pediatric amount of albuterol.

Osmotic adjusting agents which may be used include, but are not limited to, sodium chloride, potassium chloride, zinc chloride, calcium chloride and mixtures thereof. Other osmotic adjusting agents may also include, but are not limited to, mannitol, glycerol, and dextrose and mixture thereof. In an alternative embodiment, the present invention may comprise about 0.4 to about 1.0 weight percent ionic salt. Preferably, the present invention comprises about 0.9 weight percent of an osmotic adjusting agent.

In an alternative embodiment, the inhalation solution of the present invention may be prepared as follows: (i) fitting a high density polyethylene (HDPE) or stainless steel formulation tank with a bottom drain and peristaltic recirculation system (for HDPE) or tri-blender (for stainless steel) for mixing; (ii) filling the tank with approximately 90% of the required amount of Purified Water USP at a temperature of between 18° C. to 25° C.; while mixing, (iii) adding sulfuric acid, Sodium Chloride USP, and at least a therapeutically effective pediatric amount of Albuterol Sulfate USP to the tank; (iv) continue mixing until all chemical components are dissolved; (v) adding Purified Water USP to adjust the final volume, if necessary, thus producing an albuterol mixture.

Figure 6:
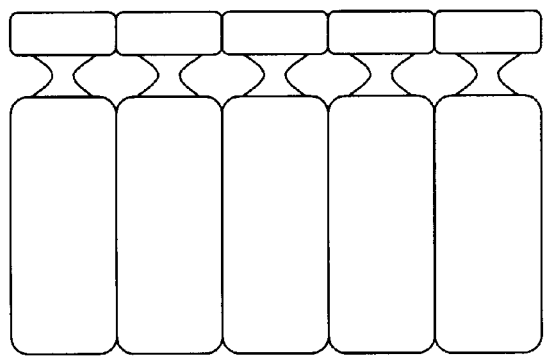
FIG. 6 depicts a non-limiting example of one or more pre-filled containers comprising the inhalation system of the present invention.

From the formulation tank, the albuterol mixture is pumped through sanitary delivery lines directly into a form-fill-seal (FFS) machine. The albuterol mixture passes through a 0.2 micron sterilizing cartridge filter, to the filling nozzles within the sterile air shower compartment, and subsequently into formed vials of low density polyethylene (LDPE). The albuterol mixture being sterile filled into the vials such that each vial contains a single unit dose of a therapeutically effective amount of albuterol. The filled vials are then sealed. The machine may form, fill and seal the vials in a continuous operation under aseptic conditions, thus producing a sterile product. For example, cards of five filled vials (FIG. 6) are overwrapped into a protective laminated foil pouch using an autowrapper machine. Five or twelve such pouches may then be packaged in a shelf carton, thus forming a prepackaged therapeutic system for relieving bronchospasm in children suffering from asthma. An appropriate label and instructions may be added in the shelf carton.

The present invention is also directed to a method of forming a unit-dose nebulizer solution comprising the step of: (i) preparing an admixture containing a therapeutically effective pediatric amount of albuterol in a pharmaceutically acceptable vehicle.

In an alternative embodiment, the present invention also comprises a device for use in the relief of bronchospasm associated with pediatric asthma. Such device may take the form of a label, written instructions or any other form incorporating indicia thereon. The device may comprise indicia which indicates that a patient suffering from bronchospasm can be treated with at least one prepackaged, sterile, premixed, premeasured and/or antimicrobial preservative-free inhalation solution comprising a unit dose of a therapeutically effective pediatric amount of albuterol in a single vial. The inhalation solution being suitable for nebulization in a nebulizer. The device also comprising indicia which provides instructions for utilizing the inhalation solution to relieve said bronchospasm in the patient.

EXAMPLES

Patients were randomized to receive a nebulizer solution comprising either 0.63 mg/3 ml or 1.25 mg/3 ml of albuterol sulfate, or a placebo. The inhalation solution was administered via a Pari LC Plus™ nebulizer and a Pari PRONEB™ compressor. Both of these products are commercially available.

In this study, qualifying children ages 6 to 12 were randomized to receive 1 of the following three treatments twice daily (TD) for 4 weeks, each in 3.0 mL volume: (1) 1.25 mg albuterol sulfate inhalation solution; (2) 9.63 mg albuterol sulfate inhalation solution; or (3) placebo (saline). Each patient was provided with a personal compressor-driven PARI LC PLUS™ nebulizer, by Pari Respirator Equipment, Inc., Richmond, Va., for the duration of the study.

A screening visit was followed by a 2-week placebo run-in phase to confirm the need for regular symptomatic beta-agonist therapy, and to give patients experience with daily diaries and peak flow measurements, as well as to demonstrate compliance. The 4-week study period began with the initial dose, to be taken in the morning, administered at the study site. Pre-dose pulmonary function tests and pulmonary function tests 30 minutes after the end of nebulization and hourly thereafter for 6 hours were performed.

After 11 days, patients returned for exchange of study medication and diaries and pulmonary function tests before and 30 minutes after the morning dosing. After completing 28 days of treatment, patients returned to the test site for a repeat of the 6-hour evaluation of safety and efficacy following administration of study medication. Diary cards were used to record asthma symptoms, night awakenings, peak flow measurements, supplemental albuterol use, change in medication and adverse events. The safety profiles of each unit dose and placebo were determined by collecting vital signs (heart rate, blood pressure, respiration rate, and body temperature) as well as electrocardiograms.

Patients

A total of 349 children (220 males and 129 females) were initially randomized, and 288 completed the double-blind 4-week treatment period. Demographic and other baseline characteristics were comparable between the three treatment groups. To be eligible for enrollment, patients had to meet the criteria described in Table 3 below.

TABLE 3

Inclusion/Exclusion Criteria

| Design Element | Description |
| --- | --- |
| Inclusion Criteria | Documented history (26 months) of moderately severe persistent asthma confirmed by a physician and requiring daily asthma medication. |
| | Generally good health apart from asthma. |
| | $FEV_1$ between 50% and 80% of predicted values at baseline and at the beginning of the double-blind treatment phase. |
| | At least 15% reversibility in $FEV_1$ following the administration of inhaled nebulized albuterol at the screening visit. |
| | Symptomatic asthma requiring the use of beta-agonists on at least 6 of the 14 days of observation during the placebo-controlled run-in-period. |
| | Willingness of patient and caregiver to provide informed consent. |
| Exclusion Criteria | Severe asthma or any serious medical condition. |
| | Use of prescription medication for which albuterol sulfate is contraindicated. |
| | Known hypersensitivity to albuterol of similar agents. |
| | Active pulmonary disease other than bronchial asthma. |
| | Upper respiratory tract infection within 4 weeks of the start of the placebo phase. |
| | Any other chronic condition that could have interfered with successful completion of the study or confounded its interpretation. |
| | Acute use of corticosteroids or other treatments which might interfere with the study within 4 weeks of the screening visit. |
| | Inability or unwillingness to perform the requirements of the protocol. |

Interventions

Patients meeting the inclusion criteria and on regularly prescribed asthma medications were permitted to continue on those medications during the course of the study if the doses remained stable. Patients were required to withhold their morning dose before each study visit and during the entire study session. After the patient completed the study session, the regularly scheduled dosing resumed for that day. All medication used to treat chronic conditions, including immunotherapy, had to be initiated at least 30 days prior to the start of the study, and the dosing regimen had to be stabilized by the initial visit. Racemic albuterol delivered by a chlorofluorocarbon (CFC) MDI or nebulizer was used on an as-needed basis as the rescue medication.

Efficacy Results

The primary efficacy endpoint was the area under the percent change from pre-dose FEV, versus time curve for the initial closing visit (Day 1) and the final closing visit (Day 28). Compared to placebo, both unit doses of albuterol produced significant improvement in FEV, following both the initial dose and the dose given at visit 4 after 4 weeks of TD treatment. The mean percent change from baseline in the area under the 6-hour curve for $FEV_1$ for both active treatment regimens compared with placebo, is shown in Table 4 (for Day 1) and Table 5 (for Day 28).

TABLE 4

% Change from Pre-Dose $FEV_1$
Intent-to-Treat Population
Day 1

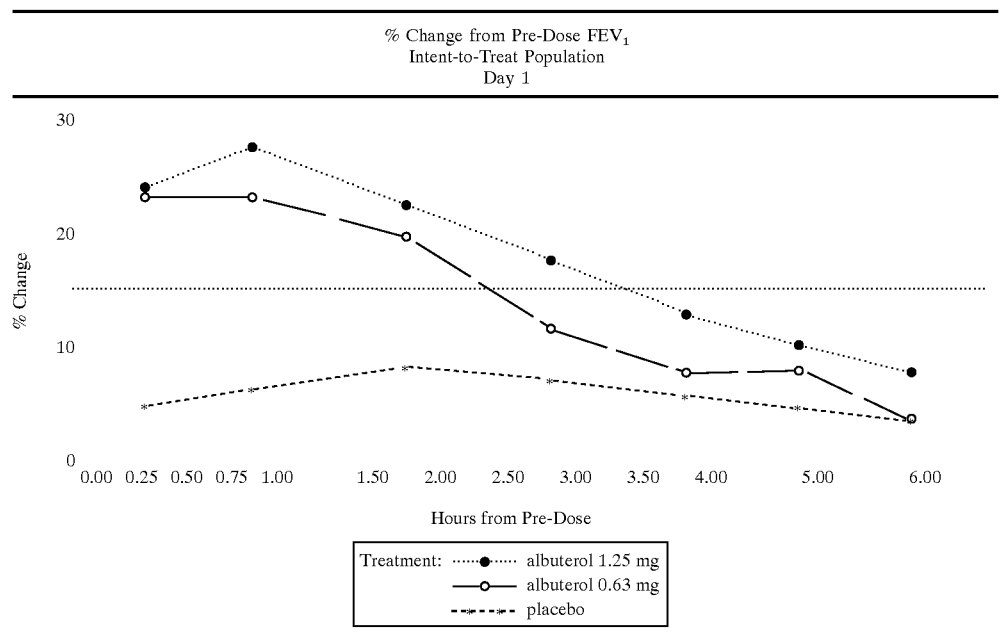

Figure 3:
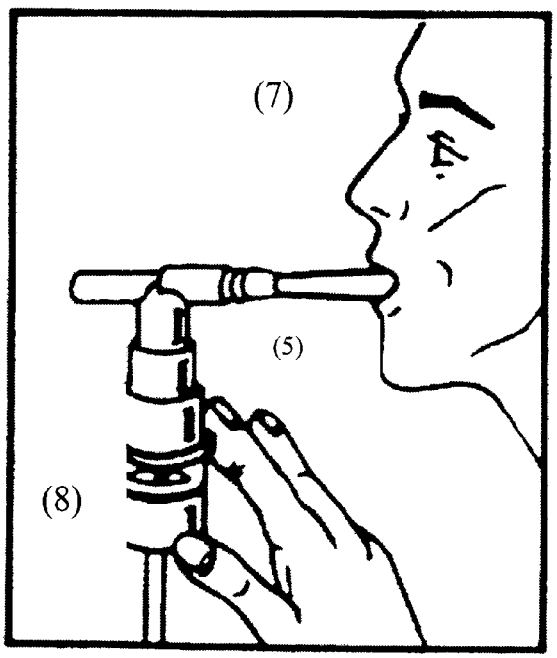

FIG. 3. Percent change in $FEV_1$ time course after treatment on Day 1.

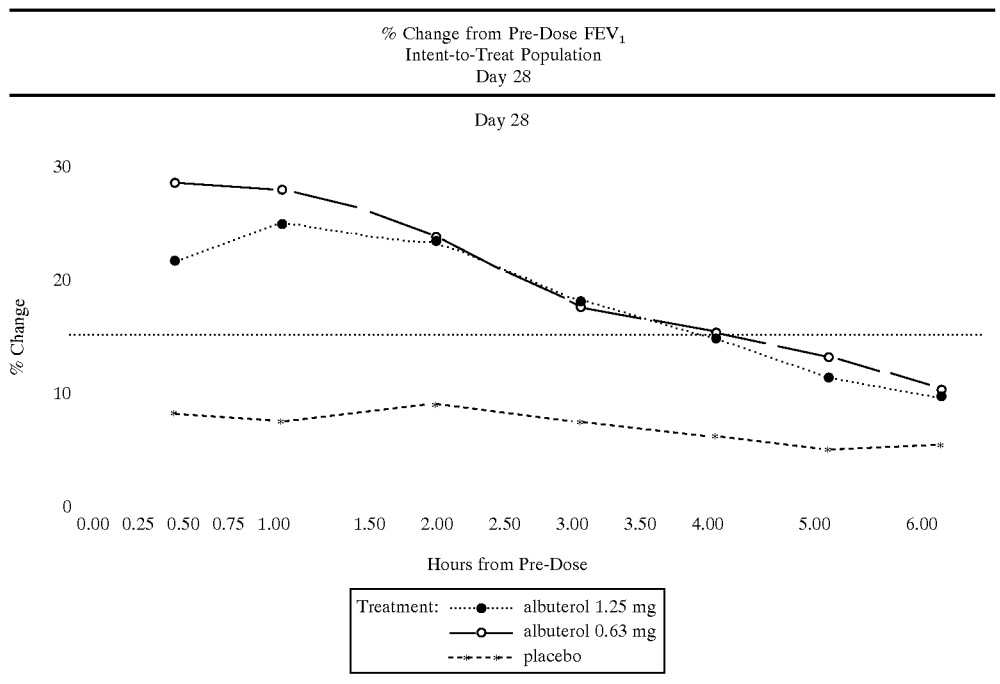

TABLE 5

% Change from Pre-Dose $FEV_1$
Intent-to-Treat Population
Day 28

Figure 4:
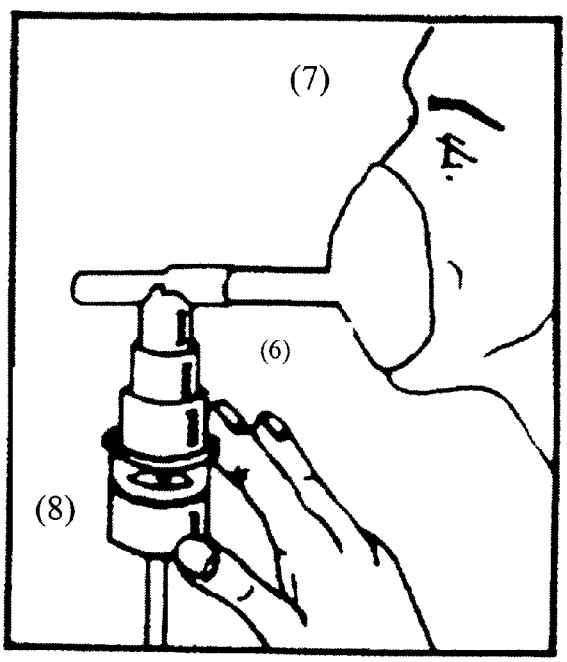

FIG. 4. Percent change in $FEV_1$ time course after treatment on Day 28.

The onset of a 15% increase in $FEV_1$ over baseline for both doses of AccuNeb was seen at 30 minutes. The mean time to speak effect was approximately 30 to 60 minutes for both doses on day 1 and after 4 weeks of treatment. The mean duration of effect, as measured by a >15% increase from baseline in $FEV_1$ was approximately 2.5 hours for both doses on day 1 and approximately 2 hours for both doses after 4 weeks of treatment. In some patients, the duration of effect was as long as 6 hours.

Subgroup analysis was performed to determine whether the overall efficacy of AccuNeb was consistent across all age, weight and disease severity groups. In all age groups, weight categories and disease severity groups, the 1.25 mg dose provided a statistically significant improvement over placebo on both Day 1 and Day 28. However, at the lower 0.63 mg dose, children 11 to 12 years of age, children heavier than 40 kg and children with more severe disease (classified as an $FEV_1 \leq 60\%$ of predicted) did not have a statistically significant improvement in $FEV_1$ over placebo at Day 29. As a result, older children, heavier children or children with more severe disease may have a better response at the 1.25 mg dose.

Safety/Tolerability

Adverse reaction information to the albuterol solution used in the study was derived from the 4-week controlled clinical trial described above. Adverse events were reported in>1% of patients receiving the present solution, more frequently than adverse events reported by patients receiving placebo, as shown in Table 6. In the study, there was one case of ST segment depression in the 1.25 mg treatment group, but no clinically relevant laboratory abnormalities related to administration were observed.

TABLE 6

Adverse Event Reports
(ADVERSE EVENTS WITH AN INCIDENCE OF 0.1% OF PATIENTS RECEIVING THE PRESENT ALBUTEROL SOLUTION AND GREATER THAN PLACEBO (EXPRESSED AS % OF TREATMENT GROUP))

|  | 1.25 mg AccuNeb (N = 115) | 0.63 mg AccuNeb (N = 117) | Placebo (N = 117) |
|---|---|---|---|
| Asthma Exacerbation | 13 | 11.1 | 8.5 |
| Otitis Media | 4.3 | 0.9 | 0 |
| Allergic Reaction | 0.9 | 3.4 | 1.7 |
| Gastroenteritis | 0.9 | 3.4 | 0.9 |
| Cold Symptoma | 0 | 3.4 | 1.7 |
| Fly Syndrome | 2.6 | 2.6 | 1.7 |
| Lymphadenopathy | 2.6 | 0.9 | 1.7 |
| Skin/Appendage injection | 1.7 | 0 | 0 |
| Urticaria | 1.7 | 0.9 | 0 |
| Migrane | 0.9 | 1.7 | 0 |
| Chest Pain | 0.9 | 1.7 | 0 |
| Bronchitis | 0.9 | 1.7 | 0.9 |
| Nausea | 1.7 | 0.9 | 0.9 |

The figures and attachments herein are presented for illustrative proposes only. They are not intended to limit the scope of the invention. Further, it should be understood that various changes and modifications to the presently preferred embodiment described herein will be apparent to those skilled in the art. Such changes and modifications can be made without departing from the spirit and scope of the present invention and without diminishing its attendant advantages. It is therefore intended that such changes and modifications be covered by the appended claims.

Also, the invention may suitably comprise, consist of or consist essentially of the elements described herein. Further, the invention described herein suitably may be practiced in the absence of any element which is not specifically disclosed herein.

We claim:

1. A method for inducing bronchodilation in a child 2–12 years of age with asthma, said method comprising the step of:

(a) administering to the child at least one single dispensing container comprising; a sterile, benzalkonium chloride-free, premixed, premeasured aqueous inhalation solution comprising an active ingredient, the active ingredient consisting essentially of a unit dose of a therapeutically effective pediatric amount of racemic albuterol sulfate; wherein the dosage of racemic albuterol sulfate is from about 0.21 mg to about 1.90 mg; the inhalation solution is suitable for nebulization in a nebulizer; wherein the inhalation solution in the at least one single container is stable, in that the inhalation solution is therapeutically effective following storage for 12 months.

2. The method of claim 1, further comprising the step of:

(a) providing indication, adverse reaction, dosage and administration data pertaining to the inhalation solution in the at least one single container; wherein the indication data informs the patient or prescriber that the inhalation solution is indicated for the relief of bronchospasm in patients 2 to 12 years of age with asthma.

3. The method of claim 2, wherein the adverse reaction data includes a list of one or more adverse events that may occur after administering the inhalation solution the adverse events comprising ottis media.

4. A method for inducing bronchodilation in a child 2–12 years of age wit asthma, said method comprising the step of:

(a) administering to the child at least one single dispensing coritainer comprising; a sterile, benzalkonium chloride-free, premixed, premeasured aqueous inhalation solution comprising an active ingredient, the active ingredient consisting essentially of a unit dose of a therapeutically effective pediatric amount of racemic albuterol sulfate; wherein the dosage of racemic albuterol sulfate is selected from the group of ranges consisting essentially of about 0.5 mg to about 0.6 mg; about 0.7 mg to about 0.8 mg; about 0.9 mg to about 1.0 mg; about 1.21 mg to about 1.40 mg; about 1.41 mg to about 1.60 mg; about 1.61 mg to about 1.80 mg; the inhalation solution in the at least one single container is suitable for nebulization in a nebulizer; wherein the inhalation solution is stable in that the inhalation solution is therapeutically effective following storage for 12 months;

(b) providing data comprising adverse reaction, dosage and administration data pertaining to the inhalation solution in the at least one single container;

(c) wherein the indication data providing that the inhalation solution is indicated for the relief of bronchospasm in patients 2 to 12 years of age with asthma;

(d) wherein the adverse reaction data provides that otitis media, asthma exacerbation, might occur after administering the inhalation solution.

5. The method of claim 2, wherein the adverse reaction data includes a list of one or more adverse events that may occur after administering the inhalation solution the adverse events comprising asthma exacerbation.

6. The method of claims 1, 2 or 3 wherein the dosage of racemic albuterol sulfate is about 0.70 mg to about 0.80 mg.

7. The method of claims 1, 2 or 3 wherein the dosage of racemic albuterol sulfate is about 1.41 mg to about 1.60 mg.

8. The method of claims 1, 2 or 3 wherein the dosage of racemic albuterol sulfate is about 0.75 mg.

9. The method of claims 1, 2 or 3 wherein the dosage of racemic albuterol sulfate is about 1.50 mg.

* * * * *

UNITED STATES PATENT AND TRADEMARK OFFICE
CERTIFICATE OF CORRECTION

PATENT NO. : 6,702,997 B2  Page 1 of 1
DATED : March 9, 2004
INVENTOR(S) : Chaudry et al.

It is certified that error appears in the above-identified patent and that said Letters Patent is hereby corrected as shown below:

Column 3,
Line 25, "tert" should be -- tert --;
Line 25, "m" should be italicized Columns 5 and 6,
Table 1, first occurrence of "C./35%" should read -- C/35% --
Table 1, second occurrence "C./35%" should read -- C/35% --

Column 7,
Line 47, "≦40 KG" should read -- ≤40 Kg --;

Column 15,
Line 53, "≦60%" should read -- ≤= 60% --;

Column 17,
Line 34, "wit" should read -- with --;
Line 36, "coritainer" should read -- "container" --;

Column 18,
Line 22, "media, asthma" should read -- media and asthma --;
Line 24, "The method of claim 2" should read -- The method of claim 1 --;
Line 27, insert -- , -- after "solution";
Lines 29, 31, 33 and 35, "The method of claims 1, 2 or 3" should read -- The method of claims 1, 2 or 4 --;

Signed and Sealed this

First Day of June, 2004

JON W. DUDAS
*Acting Director of the United States Patent and Trademark Office*